United States Patent [19]

Maksimoski et al.

[11] Patent Number: 4,983,383
[45] Date of Patent: Jan. 8, 1991

[54] HAIR CARE COMPOSITIONS

[75] Inventors: Richard C. Maksimoski, Maineville; Carolyn S. Murphy, Mason, both of Ohio

[73] Assignee: The Procter & Gamble Company, Cincinnati, Ohio

[21] Appl. No.: 427,213

[22] Filed: Oct. 31, 1989

Related U.S. Application Data

[63] Continuation-in-part of Ser. No. 274,218, Nov. 21, 1988, abandoned.

[51] Int. Cl.$^5$ .............. A61K 7/075; A61K 7/08; A61K 7/11
[52] U.S. Cl. .................. 424/70; 424/47; 424/71; 424/78; 424/DIG. 1; 424/DIG. 2; 252/DIG. 13
[58] Field of Search ............. 424/47, 70, 71, 78, 424/81, DIG. 1, DIG. 2; 252/DIG. 13

[56] References Cited

U.S. PATENT DOCUMENTS

| | | | |
|---|---|---|---|
| 2,643,375 | 6/1953 | Gant | 132/7 |
| 3,325,439 | 6/1967 | Steinbach | 260/32.8 |
| 3,681,122 | 8/1972 | Demicone et al. | 117/124 |
| 3,957,970 | 5/1976 | Korkis | 424/70 |
| 3,964,500 | 6/1976 | Drakoff | 132/7 |
| 4,185,087 | 1/1980 | Morlino | 424/70 |
| 4,221,688 | 9/1980 | Johnson et al. | 260/29.2 |
| 4,344,763 | 8/1982 | Tolgyesi et al. | 8/127.51 |
| 4,364,837 | 12/1982 | Pader | 252/173 |
| 4,387,090 | 6/1983 | Bolich, Jr. | 424/70 |
| 4,397,836 | 8/1983 | Madrange et al. | 424/47 |
| 4,450,152 | 5/1984 | Ona et al. | 424/70 |
| 4,472,375 | 9/1984 | Bolich, Jr. et al. | 424/70 |
| 4,487,883 | 12/1984 | Homan | 524/792 |
| 4,502,889 | 3/1985 | Kurita | 106/287.12 |
| 4,515,784 | 5/1985 | Bogardus et al. | 514/63 |
| 4,529,586 | 7/1985 | DeMarco et al. | 424/70 |
| 4,559,227 | 12/1985 | Chandra et al. | 424/70 |
| 4,668,508 | 5/1987 | Grollier et al. | 424/70 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 4,761,273 | 8/1988 | Grollier et al. | 424/47 |
| 4,764,363 | 8/1988 | Bolich, Jr. | 424/47 |
| 4,788,006 | 11/1988 | Bolich, Jr. et al. | 252/550 |
| 4,834,968 | 5/1989 | Bolich, Jr. | 424/47 |
| 4,842,850 | 6/1989 | Vu | 424/70 |
| 4,902,499 | 2/1990 | Bolich, Jr. et al. | 424/70 |
| 4,906,459 | 3/1990 | Cobb et al. | 424/70 |

FOREIGN PATENT DOCUMENTS

| | | |
|---|---|---|
| 1222461 | 6/1987 | Canada . |
| 116207 | 8/1984 | European Pat. Off. . |
| 155806 | 9/1985 | European Pat. Off. . |
| 288012 | 10/1988 | European Pat. Off. . |
| 56-022716 | 3/1981 | Japan . |
| 56-129300 | 10/1981 | Japan . |
| 57-162768 | 10/1982 | Japan . |
| 58-177909 | 10/1983 | Japan . |
| 61-044972 | 3/1986 | Japan . |
| 61-158914 | 7/1986 | Japan . |
| 61-161214 | 7/1986 | Japan . |
| 61-195138 | 8/1986 | Japan . |
| 2170216A | 7/1986 | United Kingdom . |

OTHER PUBLICATIONS

Chemical Abstracts, vol. 94, No. 2, May 1981, p. 373, column 1, Abstract No. 162601q.
Chemical Abstracts, vol. 97, No. 23, Dec. 1982, p. 324, column 1, Abstract No. 203098p.

*Primary Examiner*—Merrell C. Cashion, Jr.
*Assistant Examiner*—Susan S. Rucker
*Attorney, Agent, or Firm*—Gretchen R. Hatfield; Steven J. Goldstein; Richard C. Witte

[57] ABSTRACT

Hair care compositions which give both improved style and hair conditioning properties are disclosed. These compositions comprise from about 0.05% to about 10.0% of a nonrigid silicone gum, said gum having dispersed therein from about 0.01% to about 8.0% of unsolubilized particulate matter which is preferably an octylacrylamide/acrylate/butylaminoethyl methacrylate copolymer.

30 Claims, No Drawings

HAIR CARE COMPOSITIONS

This application is a continuation-in-part of Ser. No. 07/274,218 filed Nov. 21, 1988, now abandoned.

TECHNICAL FIELD

The present invention relates to hair care compositions which have improved hair conditioning and style retention properties due to the inclusion of silicone gums having dispersed therein unsolubilized particulate matter.

BACKGROUND OF THE INVENTION

The desire to have hair retain a particular shape is widely held. The two methodologies of accomplishing this are permanent chemical alteration of the hair or temporary alteration. A temporary alteration is one which can be removed by water or by shampooing. This has generally been accomplished by means of the application of a composition to dampened hair after shampooing and/or conditioning and prior to drying and/or styling. The materials used to provide setting benefits have generally been resins or gums and have been applied in the form of mousses, gels, lotions, or sprays. However, many people desire some improvement in style retention and hair volume/fullness without the necessity of a separate step. Further, some people desire a high level of style retention such as that provided by a separate composition without the negative impact that these materials generally have on dry hair properties, particularly ease of combing and hair feel.

Silicones in various hair care compositions have been disclosed in a large number of different publications, including U.S. Pat. No. 3,964,500, Drakoff, issued June 22, 1976; U.S. Pat. No. 4,364,837, Pader, issued Dec. 21, 1981; U.S. Pat. No. 4,341,799, Good, issued July 27, 1982; U.S. Pat. No. 4,465,619, Boskamp, issued Aug. 14, 1984; U.S. Pat. No. 4,515,784, Bogartus, issued May 7, 1985; U.S. Pat. No. 4,387,090, Bolich, issued June 7, 1983; and U.S. Pat. No. 4,529,586, DeMarco et al., issued July 16, 1985. U.S. Pat. No. 4,834,968, Bolich, Jr. et al., issued May 30, 1989, discloses aqueous-based hair mousse compositions which comprise silicone gums.

Hair care compositions containing hair styling polymers such as an octylacrylamide/acrylate/butylaminoethyl methacrylate copolymer have also been disclosed. Canadian Patent No. 1,222,461, Varco, issued June 2, 1987, and U.S. Pat. No. 4,397,836, Mandrange et al., issued Aug. 9, 1983, disclose hair spray compositions comprising such copolymers solubilized in alcohol. Delivery of the copolymer to hair in this form (i.e., solubilized) provides style hold benefits but leaves the hair feeling stiff and sticky. U.S. Pat. No. 4,764,363, Bolich, Jr., issued Aug. 16, 1988, discloses aerosol aqueous-based hair mousse compositions which comprise a silicone elastomer and, optionally, a hair setting polymer which may be the above-named copolymer. The polymer is again solubilized in the composition.

It has now been discovered that hair care compositions comprising certain silicone gums having dispersed therein a particulate, which is not solubilized in the composition, provide increased hair volume benefits and style retention. The compositions may be in any of the conventional forms, including but not limited to shampoos, conditioners, hairsprays, tonics, lotions, gels, and mousses. The compositions provide these benefits to the hair without negatively affecting dry hair properties such as ease of combing.

This is surprising since other silicone materials which have been typically used in hair care compositions as conditioners have decreased perceived hair volume and hurt style retention, and the resins and gums used frequently for style retention have generally hurt dry hair properties such as combing. Furthermore, the hair styling polymers like an octylacrylamide/acrylate/butylaminoethyl methacrylate copolymer, as traditionally used in hair styling compositions (i.e. solubilized therein), leave hair feeling stiff and sticky.

It is an object of the present invention to formulate hair care compositions which provide a look of increased hair volume.

It is also an object of the present invention to formulate hair care compositions which provide good style retention.

It is a further object of the present invention to formulate hair care compositions which provide good conditioning.

It is a further object of the present invention to provide an improved method of temporarily styling and conditioning hair.

It is a further object of the present invention to provide a method of treating hair for improved style retention.

These and other objects will become readily apparent from the detailed description which follows.

Unless otherwise indicated, all percentages and ratios herein are by weight.

SUMMARY OF THE INVENTION

The present invention relates to hair care compositions comprising from about 0.05% to about 10% of a nonrigid silicone gum having a viscosity of from about 1,000,000 centistoke to about 20,000,000 centistoke; said gum having dispersed therein from about 0.01% to about 8%, by weight of the composition, of unsolubilized solubilized particulate matter selected from a group of materials which will not interact with the silicone gum.

DETAILED DESCRIPTION OF THE INVENTION

The essential as well as optional components are described below.

Silicone Gum

The compositions of the present invention contain, as an essential component, a nonrigid silicone gum which when applied to hair imparts style retention and conditioning benefits.

By a nonrigid gum is meant a thick, viscous, amorphous fluid polymer where, above its glass transition temperature, it can be considered a processable, ductible flow. Ideally, this flow should be slow enough to give it the outward appearance of a solid.

The nonrigid silicone gums useful in the present invention have complex viscosities of at least about 100,000 centistoke (CSTK) and up to about 300,000,000 CSTK and, preferably from about 1,000,000 CSTK to about 20,000,000 CSTK, where complex viscosity is measured by subjecting a sample to oscillatory shear at a fixed frequency of 0.1 rad/sec at 25° C. using a Rheometric Fluids Spectrometer ® measuring films having a thickness of about 1 millimeter. The resulting viscous and elastic force responses are combined to determine the complex modulus which is divided by the imposed frequency to compute the complex viscosity.

Nonrigid silicone gums useful in the present invention include, but are not limited to, polydimethyl siloxane gums including those having end groups such as hydroxyl, cross-linked siloxanes such as organic substituted silicone elastomers, organic substituted siloxane gums including those having end groups such as hydroxyl, resin reinforced siloxanes and cross linked siloxane polymers.

The preferred nonrigid silicone gum of the present invention is polydimethyl siloxane gum having a viscosity of from about 1,000,000 CSTK to about 20,000,000 CSTK. An additional nonrigid silicone gum useful in the invention is a diphenyl-dimethyl polysiloxane gum having a molecular weight of at least about 500,000, which is diphenyl substituted to the extent of 3% or more, preferably at least about 5%, and having a viscosity of about 10,000,000 CSTK.

The gum comprises from about 0.05% to about 10%. preferably from about 0.05% to about 7%, of the hair care composition.

Non-solubilized Particulate

The present invention further comprises, as a second essential component, unsolubilized inert particulate matter. This particulate must be dispersed in the silicone gum, not solubilized in the hair care composition. Keeping the particulate unsolubilized and dispersed in the silicone gum is believed to be the key to providing the unique hair volume benefit of the hair care compositions of this invention.

It is believed that the particulate matter remains as a particulate dispersed in the gum even after the gum is mixed into a fully formulated hair care composition. When the composition is applied to hair it is believed that the silicone gum containing the particulate is deposited onto and coats the individual hair shafts. The silicone gum provides well-known hair style retention and conditioning benefits while the particles are believed to separate and hold apart the hair shafts. The result is increased hair volume without the stiff/sticky feel that is associated with most hair holding/styling products.

The particulate matter may be any non-water-soluble particulate material capable of being dispersed in the silicone gum which does not interact with the silicone in any way, e.g., through chemical reaction or bonding. That is, the particulate remains an inert dispersion in the silicone gum. Because a silica particulate will react with the silicone gum by bonding, it is not appropriate for use as the particulate matter of the present invention.

Preferably the particulate matter dispersed in the gum is of an average particle size of from about 0.1μ to about 15μ, most preferably from about 0.15μ to about 2.0μ. The particle size of the particulate matter to be dispersed into the gum may be larger than this since during the process of combining the particulate with the gum the particles may be broken down into the smaller desired particle size. Particles of this size are small enough to be easily dispersed in the gum and unnoticeable on hair but large enough to provide the increased hair volume benefit, i.e., large enough to allow for separation of the hair shafts when deposited there-between and thereon.

Any particulate material which meets the above outlined criteria may be used in the present invention. Non-limiting examples of useful particulate materials include particulate polymeric film forming/hair styling materials such as aluminum starch octenyl-succinate, sold under the tradename Dry Flo ® (available from the National Starch Company); acrylate/acrylamide copolymer sold under the tradename Ultra Hold 8 ® (available from BASF Corp.); polyvinyl methyl ether/maleic anhydride copolymer powder sold under the tradename Gantrez AN ® (available from GAF Corp.); vinyl acetate/crotonic acid copolymer sold under the tradename Luviset CA-66 ® (available from BASF Corp.). Non-polymeric particulate matter will also work in the present invention, again, as long as the material meets the requirements outlined above. Non-limiting examples of such materials are titanium dioxide, calcium carbonate and talc.

The particulate matter is included in the compositions of the present invention at a level of from about 0.01% to about 8.0%, preferably from about 0.01% to about 5.0%, by weight of the total composition.

The particulate is dispersed in the silicone gum via any conventional mixing means that will homogeneously disperse the particulate in the gum prior to mixing the gum with other components of the hair care compositions.

The preferred particulate material of the present invention is an octyl acrylamide/acrylate/butylaminoethyl methacrylate copolymer particulate. This material is present in the hair care compositions of this invention at a level of from about 0.01% to about 0.5%. This material is dispersed in the silicone gum prior to combining with any other components in the hair care compositions of the present invention, and remains unsolubilized in the final fully formulated compositions. The average particle size of this material in the gum should be from about 0.15μ to about 2.0μ.

Volatile Silicone Solvent

The compositions of the invention preferably comprise a volatile silicone solvent, or mixtures thereof, which is present at from about 0.01% to about 10%, preferably from about 0.05% to about 5.0%, of the composition. The volatile silicone solvent material allows for preservation of the dispersion of the particulate in the silicone gum while the viscosity of the gum is lowered so that it can be incorporated into various hair care products. The term "volatile" as used herein means that the material has a measurable vapor pressure.

Where the silicone gum is a polydimethyl siloxane or a polydiphenyldimethyl siloxane, the preferred silicone solvents are volatile silicones having a boiling point between about 99° C. and about 260° C. and have a solubility in water of less than about 0.1%. The degree of substitution on the siloxane (higher substitution, lower solubility) obviously affects the polymer's solubility and must be taken into account by the formulator. The silicones may be either cyclic or linear polydimethyl siloxanes. The number of silicon atoms in the cyclic silicones is about 3 to about 7, most preferably 4 or 5. The general formula for the cyclic silicones is:

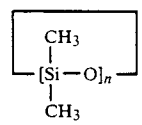

wherein n=3-7. Viscosities are generally less than about 10 centipoise (cP) at 25° C.

Linear polydimethyl siloxanes useful in the present invention generally have viscosities of less than about 5cP at 25° C. The linear volatile silicones contain from about 3 to about 9 silicone atoms and have the general formula:

$$(CH_3)_3Si—O—[Si(CH_3)_2O]_nSi\,(CH_3)_3$$

wherein n=1-7.

Silicones of the above-described types are widely available e.g., from Dow Corning as 344, 345 and 200 fluids; Union Carbide as Silicone 7202 and 7158; and Stauffer Chemical as SWS-03314.

Also useful in compositions of the present invention are certain volatile hydrocarbons. These hydrocarbons may be either straight chain or branched, and contain from about 10 to about 16 carbon atoms, preferably from about 12 to about 16 carbon atoms.

The preferred volatile silicone solvent material of the present invention is cyclomethicone available from G. E. Silicones. It is present in the compositions of the present invention at from about 0.05% to about 5.0%.

The volatile silicone solvent material is preferably combined with the silicone gum/particulate matter in several steps to further assure preservation of the dispersion. Any conventional means for mixing the two may be utilized.

Silicone Resin

An additional preferred component of the present invention is a silicone resin. Incorporation of the silicone resin into the compositions of the present invention is believed to increase the adherence of the silicone gum/particulate matter to the hair.

Silicone resins are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. The silicone resin is present in the compositions of the present invention at from about 0.01% to about 10%. A preferred resin is one offered by General Electric as GE SR545. This resin is preferably solubilized in the volatile carrier component, e.g., cyclomethicone, before combination with other hair care composition components, or the silicone gum/particulate matter.

Optional Ingredients

The hair care compositions of the present invention may be formulated in a wide variety of product types, including mousses, gels, lotions, tonics, sprays, shampoos and conditioners. The additional components required to formulate such products varies with product type and can be chosen by one skilled in the art of hair care formulation. The following is a description of some of these additional components.

Surfactants

Surfactants are preferred optional ingredients in the compositions of the invention, particularly shampoo and conditioner compositions. When present, the surfactant comprises from about 0.05% to about 50% of the composition. For a shampoo, the level is preferably from about 10% to about 30%, most preferably from about 12% to about 25%, of the composition. For conditioners the preferred level of surfactant is from about 0.2% to about 3%. Surfactants useful in compositions of the present invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae $ROSO_3M$ and $RO(C_2H_4O)_xSO_3M$ wherein R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sodium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oxide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the water-soluble salts of the organic, sulfuric acid reaction products of the general formula:

$$R_1—SO_3—M$$

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$, oleum, obtained according to known sulfonation methods, including bleaching and hydrolysis. Preferred are alkali metal and ammonium sulfonated $C_{12-18}$-n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other anionic synthetic detergents of this variety are set forth in U.S. Pat. Nos. 2,486,921; 2,486,922: and 2,396,278.

Still other anionic synthetic detergents include the class designated as succinamates. This class includes such surface active agents as disodium N-octadecylsulfosuccinamate; tetrasodium N-(1,2-dicarboxyethyl)-N-octadecylsulfo-succinamate; diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of α-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

The α-olefins from which the olefin sulfonates are derived are mono-olefins having 12 to 24 carbon atoms, preferably 14 to 16 carbon atoms. Preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific α-olefin sulfonate mixture of the above type is described more fully in the U.S. Pat. No. 3,332,880 of Phillip F. Pflaumer and Adrian Kessler, issued July 25, 1967, titled "Detergent Composition", the disclosure of which is incorporated herein by reference.

Another class of anionic organic detergents are the β-alkyloxy alkane sulfonates. These compounds have the following formula:

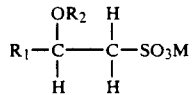

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Specific examples of β-alkyloxy-alkane-1-sulfonates, or alternatively 2-alkyloxy-alkane-1-sulfonates, having low hardness (calcium ion) sensitivity useful herein to provide superior cleaning levels under household washing conditions include: potassium-β-methoxydecanesulfonate, sodium 2-methoxy-tridecanesulfonate, potassium 2-ethoxytetradecylsulfonate, sodium 2-isopropoxyhexadecylsulfonate, lithium 2-t-butoxytetradecyl-sulfonate, sodium β-methoxyoctadecylsulfonate, and ammonium β-n-propoxydofonate.

Many additional nonsoap synthetic anionic surfactants are described in *McCutcheon's Detergents and Emulsifiers*, 1984 *Annual*, published by Allured Publishing Corporation, which is incorporated herein by reference. Also U.S. Pat. No. 3,929,678, to Laughlin et al., issued Dec. 30, 1975, discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory. 3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

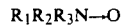

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyl-octylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyldi-methylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

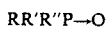

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide. 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleydimethylphosphine oxide, 2-hydroxydodecyldimethylphosphine oxide.

6. Long chain dialkyl sulfoxides containing one short chain alkyl or hydroxy alkyl radical of to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9,-trixaoctadecyl 2-hydroxyethyl sulfoxide, dodecyl methyl sulfoxide, oleyl 3-hydroxypropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Cationic surfactants useful in compositions of the present invention, particularly the conditioner compositions, contain amino or quaternary ammonium hydrophilic moieties which are positively charged when dissolved in the aqueous composition of the present invention. Cationic surfactant vehicle materials among those useful herein are disclosed in the following documents, all incorporated by reference herein: M.C. Publishing Co., *McCutcheon's Detergents & Emulsifiers*, (North American edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued June 7, 1983. If included in the compositions of the present invention, the cationic surfactant is present at from about 0.05% to about 5%.

Among the quaternary ammonium-containing cationic surfactant materials useful herein are those of the general formula:

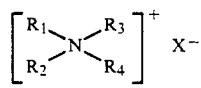

wherein $R_1$ is hydrogen, an aliphatic group of from 1 to 22 carbon atoms, or an aromatic, aryl or alkylaryl group having from 12 to 22 carbon atoms; $R_2$ is an aliphatic group having from 1 to 3 carbon atoms, and X is an anion selected from halogen, acetate, phosphate, nitrate and alkylsulfate radicals. The aliphatic groups may contain, in addition to carbon and hydrogen atoms, ether linkages, and other groups such as amino groups.

Other quaternary ammonium salts useful herein are of the formula:

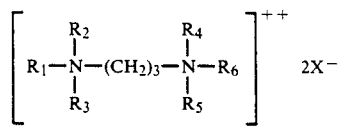

wherein $R_1$ is an aliphatic group having from 16 to 22 carbon atoms, $R_2$, $R_3$, $R_4$, $R_5$, and $R_6$ are selected from hydrogen and alkyl having from 1 to 4 carbon atoms, and X is an ion selected from halogen, acetate, phosphate, nitrate and alkyl sulfate radicals. Such quaternary ammonium salts include tallow propane diammonium dichloride.

Preferred quaternary ammonium salts include dialkyldimethylammonium chlorides, wherein in the alkyl groups have from 12 to 22 carbon atoms and are derived from long-chain fatty acids, such as hydrogenated tallow fatty acid. (Tallow fatty acids give rise to quaternary compounds wherein $R_1$ and $R_2$ have predominately from 16 to 18 carbon atoms.) Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(-hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Ditallow dimethyl ammonium chloride, dicetyl dimethyl ammonium chloride, stearyl dimethyl benzyl ammonium chloride and cetyl trimethyl ammonium chloride are preferred quaternary ammonium salts useful herein. Di-(hydrogenated tallow) dimethyl ammonium chloride is a particularly preferred quaternary ammonium salt.

Salts of primary, secondary and tertiary fatty amines are also preferred cationic surfactant vehicle materials. The alkyl groups of such amines preferably have from 12 to 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, myristyl amine, tridecyl amine, ethyl stearylamine, N-tallowpropane diamine, ethoxylated (5 moles E.O.) stearylamine, dihydroxy ethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate and N-tallowpropane diamine dichloride and stearamidopropyl dimethylamine citrate. Cationic amine surfactants included among those useful in the present invention are disclosed in U.S. Pat. No. 4,275,055, Nachtigal, et al., issued June 23, 1981 (incorporated by reference herein).

Zwitterionic surfactants, useful in shampoos as well as conditioners, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

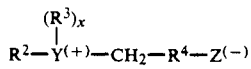

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl) carboxymethyl betaine, stearyl bis-(2-hydroxy-propyl) carboxymethyl betaine, oleyl dimethyl gamma-carboxypropyl betaine, lauryl bis-(2-hydroxypropyl)alphacarboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. The alkyl sulfates, the ethoxylated alkyl sulfates and mixtures thereof are preferred for use herein.

Gel Vehicle Materials

Where the hair care compositions are conditioner compositions, preferred optional components include gel vehicle materials. The vehicle comprises two essential components: a lipid vehicle material and a cationic surfactant vehicle material. Such gel-type vehicles are generally described in the following documents, all incorporated by reference herein: Barry, "The Self Bodying Action of the Mixed Emulsifier Sodium Dodecyl Sulfate/Cetyl Alcohol", 28 *J. of Colloid and Interface Science* 82–91 (1968); Barry, et al., "The Self-Bodying Action of Alkyltrimethylammonium Bromides/Cetostearyl Alcohol Mixed Emulsifiers; Influence of Quaternary Chain Length", 35 *J. of Colloid and Interface Science* 689–708 (1971); and Barry, et al., "Rheology of Systems Containing Cetomacrogol 1000 Cetostearyl Alcohol, I. Self Bodying Action", 38 *J. of Colloid and Interface Science* 616–625 (1972).

Lipid vehicle material

The vehicles may incorporate one or more lipid materials (herein referred to as comprising a "lipid vehicle material", singly or in combination), which are essentially water-insoluble, and contain hydrophobic and hydrophilic moieties. Lipid vehicle materials include naturally or synthetically-derived acids, acid derivatives, alcohols, esters, ethers, ketones, and amides with carbon chains of from 12 to 22, preferably from 16 to 18, carbon atoms in length. Fatty alcohols and fatty esters are preferred; fatty alcohols are particularly preferred.

Lipid vehicle materials among those useful herein are disclosed in *Bailey's Industrial Oil and Fat Products*, (3rd edition, D. Swern, ed. 1979) (incorporated by reference herein). Fatty alcohols included among those useful herein are disclosed in the following documents, all incorporated by reference herein: U.S. Pat. No. 3,155,591, Hilfer, issued Nov. 3, 1964; U.S. Pat. No. 4,165,369, Watanabe, et al., issued Aug. 21, 1979; U.S. Pat. No. 4,269,824, Villamarin, et al., issued May 26, 1981; *British Specification No.* 1,532,585, published Nov. 15, 1978; and Fukushima, et al., "The Effect of Cetostearyl Alcohol in Cosmetic Emulsions", 98 *Cosmetics & Toiletries* 89–112 (1983). Fatty esters included among those useful herein are disclosed in U.S. Pat. No. 3,341,465 Kaufman, et al., issued Sept. 12, 1976 (incorporated by reference herein). If included in the compositions of the present invention, the lipid vehicle material is present at from about 0.1% to about 10.0%.

Preferred esters for use herein include cetyl palmitate and glycerylmonostearate. Cetyl alcohol and stearyl alcohol are preferred alcohols. A particularly preferred lipid vehicle material is comprised of a mixture of cetyl alcohol and stearyl alcohol containing from about 55% to about 65% (by weight of mixture) of cetyl alcohol.

Other vehicles, suitable for use with the nonrigid silicone gum/particulate matter of the present invention are, for example, tonics, mousses, gels and hairsprays. Tonics, gels and non-aerosol hairsprays utilize a solvent such as water or alcohol while mousses and aerosol hairsprays additionally utilize a propellant such as trichlorofluoromethane, dichlorodifluoromethane, dichlorotetrafluoroethane, monochlorodifluoromethane, trichlorotrifluoroethane, dimethylether, propane, n-butane and isobutane, used singly or admixed, in addition to the nonrigid silicone gum/particulate matter. The level of propellant can be adjusted as desired but is generally from about 3% to about 30% of the mousse composition and from about 15% to about 50% of the aerosol hairspray composition. A tonic or hairspray product having a low viscosity preferably requires an emulsifying agent to keep the silicone gum/particulate matter homogeneously dispersed in solution. Examples of suitable emulsifying agents include nonionic, cationic, and anionic surfactants. Examples of such materials are described supra.

Preferably co-surfactant systems are utilized. For example, combinations of anionic and nonionic surfactants or cationic and nonionic surfactants. Generally, combinations of anionic and cationic surfactants will not provide the appropriate emulsifying benefits. If such an emulsifying agent is present, it is generally present at a level of from about 0.25% to about 7.5% of the composition. The specific surfactant materials or combinations of surfactant materials to be used and the particular levels of use are determined by those that will allow the formation of microemulsions or microsuspensions of the silicone gum/particulate in the composition. An example of a preferred surfactant emulsifier system is the combination of lauramine oxide and cocamide DEA.

Hairspray compositions of the present invention are particularly difficult to formulate because silicone gum is not soluble in typical hairspray solvents, such as ethanol. Hence, the silicone gum tends to precipitate out of solution over time and form a solid mass at the bottom of the container. This solid mass is un-redispersible in the solvent upon agitation. Use of the above described surfactant emulsifying agents provides one solution to this problem. Selection of appropriate emulsifying agents will enable the formation of a stable microemulsion of the silicone gum material in the hairspray composition. With such a method the silicone gum does not phase-separate. Hence, the problems of dispersion/agglomeration are avoided.

An alternate way of formulating the hairspray form of the compositions of the present invention is to use a hydrophobically-treated clay as a suspending/anti-agglomerating agent for the silicone gum. Use of these selected clays will avoid precipitation of the silicone gum out of solution and agglomeration of the silicone gum into a solid un-redispersible mass. Though hairspray compositions formulated with these clay materials will still separate into two phases (a volatile carrier phase and a silicone gum phase) over time, the presence of the clay materials allows for redispersion of the silicone gum in the volatile carrier with a gentle shake of the container.

These clay materials have been used in the past as suspending agents for personal care compositions which contain particulate materials. For example, EPO Patent Application No. 0 028,853, Beckmeyer et al., published May 20, 1981, discloses antiperspirant compositions comprising particulate antiperspirant salts, silicone fluids, and bulking/suspending agents which may be hydrophobically-modified clays. See also U.S. Pat. No. 4,840,786, Johnson et al, issued June 20, 1989, U.S. Pat. No. 4,152,416, Spitzer et al., issued May 1979, discloses antiperspirant compositions comprising antiperspirant salts, silicone gums, and bulking agents which may be collodial silica or hydrophobic clays.

The suspending/anti-agglomerating agents useful herein include hydrophobically-treated montmorillonite clays, e.g., bentonites and hectorites. Untreated clays will not provide the same suspending/anti-agglomerating benefits in the present invention The hectorite and bentonite hydrophobically-treated clay minerals of the instant compositions can be described as expandable (swellable), three-layer clays, in which a sheet of aluminum/oxygen atoms or magnesium/oxygen atoms lies between two layers of silicone/oxygen atoms, i.e., aluminosilicates and magnesium silicates, having an ion exchange capacity of at least about 50 meq/100 g of clay, and preferably at least about 60 meq/100 g of clay. The term "expandable" as used to describe clays relates to the ability of the layered clay structure to be swollen or expanded on contact with water. Such hectorite and bentonite clays are described in Grim, *Clay Mineralogy* (2nd. Ed.) pp. 77–79 (1968), and in Van Olphen, *An Introduction to Clay Colloid Chemistry*, (2nd. Ed.) pp. 64–76 (1977), both of which are incorporated by reference herein.

The clay minerals employed in the compositions of the instant invention contain exchangeable cations including, but not limited to, protons, sodium ions, potassium ions, calcium ions, magnesium ions, lithium ions, and the like.

It is customary to distinguish between clays on the basis of one cation predominantly or exclusively absorbed.

Several of these hydrophobically-treated clay agents are commercially available. They include, for example, quaternium-18 bentonite, sold under the tradenames Bentone-34 ® by NL Chemicals and Tixogel VP ® by United Catalysts; quaternium-18-hectorite, sold under the tradename Bentone-38 ® by NL Chemicals; stearalkonium bentonite, sold under the tradename Tixogel-VZ ® by United Catalysts; and stearalkonium hectorite, sold under the tradename Bentone-27 ® by NL Chemicals.

A small amount of water is required in the hairspray compositions of the present invention to activate the clay agent. Generally this requirement can be met by using a 190-proof ethanol solvent for the system. Alternatively, a small amount of water can be added to the composition.

The present compositions in the form of a hairspray comprise a volatile carrier system. This can comprise any of those conventionally used in resin hairspray formulations, preferably a $C_1$-$C_6$ alkanol, most preferably ethanol. This component "carries" the silicone gum to the hair than volatilizes, leaving the particulate containing gum behind on the hair to provide hair conditioning, hair volumizing benefits, and hairstyling hold. The carrier is present in the hairspray composition at from about 20% to about 95%, preferably from about 35% to about 95%, by weight of the composition. Water can also be used to substitute for part of the volatile carrier component.

The hairspray compositions of the present invention will comprise from about 0.05% to about 10% of a non rigid silicone gum having a viscosity of from about 1,000,000 centistoke to about 20,000,000 centistoke; said gum having dispersed therein from about 0.01% to about 8%, by weight of the composition, of unsolubilized particulate matter selected from a group of materials which will not interact with the silicone gum, as described supra: from about 0.05% to about 5.0%, preferably from about 0.05% to about 2.0%, of a hydrophobically-modified clay suspending/antiagglomerating agent; and a volatile carrier.

An additional component, that is preferably used in the hairspray compositions of the present invention, is a hair setting polymer. Any polymer soluble or dispersible in the volatile carrier or solvent phase may be used. Solubility/dispersibility is determined at ambient conditions (e.g., temperature about 25° C. and atmospheric pressure). Suitable types of polymers include anionic, nonionic, amphoteric and cationic. Specific polymers include polyvinylpyrrolidone (PVP), copolymers of (PVP) and methylmethacrylate, copolymers of PVP and vinylacetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether maleic acid), and octylacrylamide/acrylate/butylaminoethyl methacrylate copolymers. PVP and PVP copolymers with other monomers are preferred. Mixtures of polymers may also be used.

These hair hold resins can be the same as those used as the particulate material dispersed in the silicone gum of the present invention. Though the material may be the same, it is providing two separate functions in the present compositions. When it is dispersed as a particulate in the gum it prevents over-conditioning of the hair by the silicone gum and may provide hair volumizing benefits to the composition, as discussed supra. When the hair-hold or hair-setting polymer is solubilized in the volatile carrier or solvent it is providing a traditional style holding benefit to the present hair spray composition. Though the silicone gum (having the particulate dispersed therein) provides soft hair feel, increased hair manageability, and increased hair volume benefits, it does not, itself, provide significant hair hold, hence, the need for a separate hair style/hold agent. These various components provide the user of the present compositions with a hairspray which after application provides hair styling, but with a softer feel to hair than traditional hair spray products provide.

With certain of the polymers it may be necessary to neutralize some acidic groups to promote solubility/dispersibility (e.g., PVA/crotonic acid). Examples of suitable neutralizing agents include 2-amino-2-methyl -1,3-propanediol (AMPD); 2-amino-2-ethyl-1,3 propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol amine (DIPA); triisopropanolamine (TIPA); and dimethyl stearamine (DMS).

When present the polymer(s) is used at a level of from about 0.25% to about 20%, preferably from about 1% to about 20%, of the total composition. The mass average molecular weight of the polymer is not critical, but is generally in the range of from about 2,000 to about 2,000,000.

The hair care compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; thickeners and viscosity modifiers such as a diethanolamide of a long chain fatty acid (e.g., PEG 3 lauric diethanolamide), cocomonoethanol amide, dimethicone copolyols, guar gum, methyl cellulose, starches and starch derivatives; fatty alcohols such as cetearyl alcohol; sodium chloride; sodium sulfate; polyvinyl alcohol; ethyl alcohol; pH adjusting agents such as citric acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts; hair reducing agents such as the thioglycolates; perfumes; sequestering agents such as disodium ethylenediamine tetra-acetate; and polymer plasticizing agents such as glycerin and propylene glycol. Such optional ingredients generally are used individually at a level of from about 0.01% to about 10.0%, preferably from about 0.05% to about 5.0% by weight of the composition.

When the hair care compositions of the present invention are formulated into shampoos, the level of the nonrigid silicone gum incorporated therein ought to be from about 0.1% to about 4.0% and the level of particulate matter ought to be from about 0.01% to about 1.0 %. For a hair conditioning product the respective levels of these components ought to be from about 0.05% to about 2.0% gum and from about 0.01% to about 0.5% particulate. For hair tonic the respective levels of these components out to be from about 0.01% to about 2.0% gum and from about 0.01% to about 0.5% particulate.

The pH of the present compositions is between about 3 and about 7, preferably between about 6 and about 7.

Keeping the pH on the acidic side prevents solubilization of the particulate out of the gum and into the exterior phase.

As with all compositions, the present compositions should not contain components which unduly interfere with the performance of the compositions.

METHOD OF MAKING

The hair care compositions of the present invention can be made using any conventional formulations and mixing techniques. However, it is critical that the particulate matter be dispersed in the silicone gum prior to combination with the other hair care composition components. If a volatile carrier is used in the compositions of the present invention to lower the viscosity of the silicone gum, it is preferably combined with the silicone gum in several steps. Mixing the volatile carrier and silicone gum together this way avoids disruption of the homogeneous dispersion of the particulate matter in the gum. If a silicone resin is also used in the composition, it should preferably be mixed with the volatile carrier prior to combination of the carrier material with the gum. The resulting mixture can then be formulated into a variety of hair care products including tonics, shampoos, conditioners, mousses, gels and hair sprays. Preferably the pH of the final composition is adjusted, if necessary, to be between 3 and 7, preferably between 6 and 7.

Methods of making various types of hair care compositions are described more specifically in the following examples.

METHOD OF USE

The hair care compositions of the present invention are used in conventional ways to provide the hair conditioning/styling/holding benefits of the present invention. Such method of use depends upon the type of composition employed but generally involves application of an effective amount of the product to the hair, which may then be rinsed from the hair (as in the case of shampoos and some conditioning products) or allowed to remain on the hair (as in the case of spray, mousse, gel, and tonic products). By "effective amount" is meant an amount sufficient to provide the hair volume benefits desired considering the length and texture of the hair, and the type of product used. Preferably the product is applied to wet or damp hair prior to drying and styling of the hair. Use of the compositions of the present invention in this manner provides optimum hair holding, and volumizing benefits. After the compositions of the present invention are applied to the hair, the hair is dried and styled in the usual ways of the user.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLE I

| Silicone Gum/Particulate Premix | |
|---|---|
| Component | Weight % |
| *Premix A* | |
| Dimethicone[1] | 80 |
| Octylacrylamide/Acrylate/Butyl Aminoethyl Methacrylate Copolymer Particulate[2] | 20 |
| *Premix B* | |
| Cyclomethicone[3] | 50 |
| Silicone Resin[4] | 50 |

[1] High viscosity (>1,000,000 CSTK) silicone gum available from G.E. Silicones.
[2] AMPHOMER ® polymeric particulate (having an original particle size range of 75-200 microns) available from National Starch.
[3] Cyclomethicone having a D5 structure available from G.E. Silicones.
[4] Available from G.E. Silicones.

Using a mixer such as a ribbon type blender, the premix A components are combined and mixed until dispersed and until the AMPHOMER particulate has been pulverized to particles having an average diameter of between $0.15\mu$ and $2.0\mu$. Using a separate mixing vessel, the premix B components are mixed until homogeneous. Premix A and premix B are then combined at a ratio of 57% A to 43% B and mixed until homogeneous.

The premix solution is then diluted as follows using a mixing vessel with a high speed/torque agitation system. The premix solution is mixed with additional premix B at a ratio of 70.175% premix solution to 29.825 premix B until homogeneous. The premix solution formed is mixed with additional premix B at a ratio of 50% premix solution to 50% premix B until homogeneous. This silicone gum/particulate premix can be used to make a variety of hair care products as illustrated in the following examples.

In each of the following examples the dimethicone gum is a high viscosity (>1,000,000 CSTK) silicone gum available from G.E. Silicones and the Octylacrylamide/Acrylate/Butylaminoethyl Methacrylate Copolymer Particulate is AMPHOMER ® polymeric particulate having an original particle size range of 75-250 microns available from National Starch which when dispersed in the silicone gum is pulverized such that the particle size range is reduced to from about $0.15\mu$ to about $2.0\mu$.

EXAMPLE II

| Non-Aerosol Hair Tonic Spray | |
|---|---|
| Component | Weight % |
| PVP/VA Copolymer | 2.00 |
| Lauramine Oxide | 1.00 |
| Cocamide DEA | 0.80 |
| Carbomer 956 | 0.20 |
| Potassium Hydroxide | to adjust pH to between 6 and 7 |
| Premix from Example I | 0.25 |
| Fragrance | Q.S. |
| Preservative | Q.S. |
| Water | Q.S. |

A non-aerosol hair tonic spray product is prepared as follows The lauramide oxide is mixed with part of the water at a ratio of 4 to 1 with, for example, a ribbon type mixer until homogeneous. The cocamide DEA is added and mixed until homogeneous. The premix from Example I is added and mixed until homogeneous.

The remainder of the water is put into a stainless steel mixing vessel. The Carbomer 956 is mixed into the water using, for example, a triblender or eductor mixer. Mixing is continued until the Carbomer is completely dissolved. The potassium hydroxide is added while mixing.

The premix is added while mixing until homogeneous. The PVP/VA is then added and mixing is continued until the batch is homogeneous. The preservative is added and mixing is continued until homogeneous. The perfume is added and mixing is continued for an additional 10 minutes. Once the batch is well-mixed homogenization of the batch is performed using conventional apparatus. The final product is an opaque liquid having a pH of about 6 and 7.

This hair tonic is sprayed onto damp hair and the hair is then styled/dried. The amount of tonic used will depend on the volume/hold benefits desired and the amount of hair being treated as well as the texture of the hair. Use of this product on the hair provides a look of increased hair volume. The feel of the hair is desirably soft and manageable, not stiff and sticky as is the result with most hair styling products. The hold of the style is long listing as well.

EXAMPLE III

Shampoo Examples

| Component | Weight % A | B |
|---|---|---|
| Ammonium Lauryl Sulfate | 13.5 | 13.5 |
| Ammonium Laureth Sulfate | 4.0 | 4.0 |
| Ammonium Xylene Sulfonate | 0.1 | 0.1 |
| Dimethicone Gum[2] | 0.16 | 0.80 |
| Octylacrylamide/Acrylate/Butyl Aminoethyl Methacrylate Copolymer particulate[2] | 0.04 | 0.20 |
| Silicone Resin[1,2] | 0.40 | 2.00 |
| Cyclomethicone[1,2] | 0.40 | 2.00 |
| Perfume | 1.20 | 1.20 |
| Preservative | 0.033 | 0.033 |
| Cocoamide MEA | 4.0 | 4.0 |
| Ethylene Glycol Distearate | 2.0 | 2.0 |
| Cetearyl Alcohol | 0.60 | 1.00 |
| Sodium Citrate | 0.05 | 0.05 |
| Citric Acid | 0.05 | 0.05 |
| Sodium Hydroxide | 0.01 | 0.01 |
| Sodium Chloride | 1.0 | 1.0 |
| Water | Q.S. | Q.S. |

[1]Supplied by G.E. Silicones
[2]These compenents are combined in a silicone premix, e.g., as described in EXAMPLE I.

Shampoo Processing

Ammonium lauryl sulfate, citric acid, sodium citrate and sodium hydroxide are added to the distilled water at about 15° C. The mixture is heated to from 70° C. to 80° C. The cocamide MEA and glycol distearate are added at this point. The ammonium laureth-3 sulfate, cetearyl alcohol and silicone premix are blended at 70° C. to 90° C. This mixture is added to the batch following the glycol distearate. The preservative and fragrance are then added. The batch is mixed for 5 minutes, then milled under high shear using conventional milling apparatus and then cooled to room temperature (15° C. to 25° C.). Sodium chloride and ammonium xylene sulfonate are added for viscosity control as needed. The final compositions have a pH of from about 5.0 to about 6.0.

These compositions are used in the same way one would use a standard shampoo. The hair is then dried and styled in the usual way. When used in this way, the compositions provide hair with effective cleaning, conditioning and styling, as well as a look of increased volume.

EXAMPLE IV

Conditioner Examples

| Component | Weight % A | B |
|---|---|---|
| Cyclomethicone[1,2] | 4.41 | 3.90 |
| Cetyl Alcohol | 1.0 | 1.0 |
| Quaternium 18 | 0.85 | 0.85 |
| Stearyl Alcohol | 0.75 | 0.75 |
| Hydroxyethyl Cellulose | 0.50 | 0.50 |
| Stearimidopropyl Dimethylamine | 0.50 | 0.50 |
| Ceteareth-20 | 0.35 | 0.35 |
| Glyceral Monstearate | 0.25 | 0.25 |
| Fragrance | 0.25 | 0.25 |
| Dimethicone Gum[2] | 0.10 | 0.40 |
| Silicone Resin[1,2] | 0.40 | 1.00 |
| Citric Acid | 0.13 | 0.13 |
| Dimethicone Copolyol | 0.10 | 0.10 |
| Octyl Acrylamide/Acrylate/Butyl Aminoethyl Methacrylate Copolymer particulate[2] | 0.04 | 0.10 |
| Preservative | 0.033 | 0.033 |
| Water | Q.S. | Q.S. |

[1]Supplied by G.E. Silicones
[2]These components are combined as a premix, e.g., as described in Example I.

Conditioner Processing

Hydroxyethyl cellulose is added to the distilled water at a temperature of 15° C. to 40° C. This mixture is well-dispersed, then heated to a temperature of from 60° C. to 90° C. Materials 2 through 8 are added to the batch while the temperature is maintained in this range. The mixture is stirred for approximately 10 minutes, then cooled to approximately 50° C. The remaining materials are added at this temperature. The mixture is milled under high shear for approximately 2 minutes using a conventional milling apparatus, then cooled to room temperature. The finished compositions have a pH of from about 3.5 to about 4.5.

These compositions are used as one would use standard rinse-type conditioning products, i.e., after shampooing, the conditioner is applied to the hair, allowed to stay on the hair for at least about one minute, and then rinsed from the hair. The hair is then dried and styled in the usual way. When used in this way, these compositions provide hair with effective conditioning, styling and a look of increased volume.

EXAMPLE V

Mousse Compositions

| Component | Weight % A | B |
|---|---|---|
| A-46 propellant[1] | 7.50 | 7.50 |
| PVP/VA Copolymer (50% active) | 1.00 | 2.50 |
| Lauramine Oxide | 1.00 | 1.00 |
| Cocamide DEA | 0.80 | 0.80 |
| Silicone Resin[2,3] | 0.15 | 0.40 |
| Dimethicone Gum[3] | 0.10 | 0.40 |
| Cyclomethicone[2,3] | 0.40 | 2.00 |
| Octyl Acrylamide/Acrylate/Butyl Aminoethyl Methacrylate Copolymer particulate[3] | 0.04 | 0.80 |
| Preservative | Q.S. | Q.S. |
| Fragrance | Q.S. | Q.S. |
| Water | Q.S. | Q.S. |

[1] A mixture of propane (20%), isobutane (78%) and n-butane (2%)
[2] Supplied by G.E. Silicones
[3] These components are combined in a premix as in Example I.

The gel compositions of the present invention are prepared using the method outlined in Example II for the hair tonic, except that the Carbomer 940 is substituted for the Carbomer 956 and the triethanolamine is added before the preservative and mixed in until homogeneous. These compositions have a pH of about 6 to 7.

These compositions are used in the same way as the mousse compositions of Example V. When used in this way, these gel compositions provide effective conditioning, styling and a look of increased volume to hair.

The aerosol mousses of the present invention are prepared by combining all ingredients except the aerosol propellant into a batch called the concentrate. This concentrate is made by combining with agitation all of the ingredients except for the preservative and the premix prepared as in Example I, and mixing until well dispersed. The preservative and premix are finally added and mixing continued until these are thoroughly dispersed. The resulting mixture is then homogenized using conventional apparatus. The resulting concentrate has a pH of from 6 to 7. Aerosol mousse cans are prepared by placing 135 grams of concentrate into 5 oz. aluminum epoxy lined cans, placing mousse valves on can tops, drawing a vacuum to evacuate can headspace (to remove air), and crimping the valves into place. The propellant (15 grams) is added by pressure filling through the valve stem.

These compositions are massaged into clean/damp hair and the hair is then dried and styled. The amount of mousse used will depend on the volume/hold benefits desired and the amount of hair being treated as well as the texture of the hair. When used in this way, these mousse compositions provide effective conditioning, styling and a look of increased volume of hair.

EXAMPLE VI

Gel Compositions

| Component | Weight % A | B |
|---|---|---|
| PVP/VA Copolymer | 1.00 | 2.50 |
| Lauramine Oxide | 1.00 | 1.00 |
| Cocamide DEA | 0.80 | 0.80 |
| Carbomer 940 | 0.40 | 0.60 |
| Triethanolamine | 0.36 | 0.56 |

-continued

| | | |
|---|---|---|
| Silicone Resin [1,2] | 0.15 | 0.20 |
| Dimethicone Gum [2] | 0.10 | 0.40 |
| Cyclomethicone [1,2] | 0.02 | 0.40 |
| Octyl Acrylamide/Acrylate/Butyl Aminoethyl Methacrylate Copolymer particulate [2] | 0.01 | 0.10 |
| Preservative | Q.S. | Q.S. |
| Fragrance | Q.S. | Q.S. |
| Water | Q.S. | Q.S. |

[1] Supplied by G.E. Silicones.
[2] These components are combined in a premix as in Example I.

EXAMPLE VII

Non-Aerosol Silicone Hairspray

| Component | Weight % |
|---|---|
| Ethanol (190 proof) | 87.439 |
| PVP/VA copolymer (50/50) | 10.00 |
| Cyclomethicone[1] | 1.60 |
| Dimethicone copolyol[2] | 0.50 |
| Amphomer[3] particulate | 0.05 |
| Tixogel VP[4] | 0.10 |
| Polydimethysiloxane gum[5] | 0.20 |
| Octyl Salicylate | 0.01 |
| Keratin AMino Acids | 0.001 |
| Fragrance | 0.10 |
| | 100% |

[1] Cyclomethicone having a $D^5$ structure available from GE Silicones
[2] FF400 Dimethicone Copolyol available from Dow Corning
[3] Octylacrylamide/Acrylate/Butyl Aminoethyl Methacrylate Copolymer having an original particle size (before milling) of 75-200 microns, available from National Starch
[4] Quaternium 18-Bentonite available from United Catalysts
[5] SE-30 Gum available from GE Silicones The Amphomer ® particulate is first dispersed in the polydimethyl siloxane gum using a dough style mixer at low speed for about 4 hours. The Amphomer ®/gum mixture is then added to the cyclomethicone and mixed until dissolved using a dough style mixer for about 8 hours. The dimethicone copolyol is added and the composition mixed using the dough style mixer until homogeneous. The Tixogel ® is then added and mixed using the dough style mixer until homogeneous. Using a Tek Mar ® mill the composition is slowly milled with the ethanol until homogeneous. Using conventional mixing the PVP/VA/copolymer is added. The octyl salicylate, keratin amino acids, and fragrance are mixed into the composition in that order. The resulting hairspray provides improved hair conditioning and volumizing benefits with a softer feeling hair hold. Substantially similar results are obtained when an equivalent amount of a quaternium-18-hectorite (for example, the material sold under the trade name Bentene-38 ® by NL Chemicals), a stearalkonium bentonite (for example, the material sold under the trade name Tixogel VZ ® by United Catalysts), or a stearaldonium hectorite (for example, the material sold under the trade name Bentone-27 ® by NL Chemicals), is substituted for the Tixogel VP ® clay.

EXAMPLE VIII

Aerosol Silicone Hairspray

An aerosol silicone hairspray can be prepared by combining the composition of Example I with a propellant, for example, A-31 propellant, which is an isobutane propellant available from Phillips Petroleum, Inc., at a ratio of 3 parts hairspray composition to 1 part propellant.

EXAMPLE IX cl Hairspray Composition

| Hairspray Composition | |
|---|---|
| Component | Weight % |
| SD40 Alcohol | 87.29 |
| Premix 1 | 2.3 |
| PVP/VA Copolymer | 10.00 |
| Dimethicone Copolyol[1] | 0.30 |
| Octyl Salicylate | 0.01 |
| Keratin Amino Acids | 0.001 |
| Perfume | 0.10 |
| | 100% |

| Premix 1 | |
|---|---|
| Component | Weight % |
| D5 Cyclomethicone[2] | 4.35 |
| Siloxane Resin[3] | 4.35 |
| Polydimethylsiloxane Gum[4] | 1.74 |
| Amphomer ® 5 | 0.43 |
| DRO Water | 10.87 |
| Lauramine Oxide | 43.48 |
| Cocamide DEA | 34.78 |
| | 100% |

[1] FF400 Dimethicone Copolyol, available from Dow Corning
[2] Cyclomethicone having a D5 structure, available from GE Silicones
[3] GE SR545, available from GESilicones
[4] SE-76 gum, available from General Electric Co.
[5] Octylacrylamide/Acrylate/Butyl Aminoethyl Methacrylate Copolymer having an original particle size (before milling) of 75-200 microns, available from National Starch The Amphomer ® is first dispersed into the Polydimethyl Siloxane Gum using a dough-style mixer at a low shear speed for about 4 hours. The Amphomer ® /gum mixture is then added to the cyclomethicone and siloxane resin and mixed until dissolved using a dough style mixer for about 8 hours. The DRO water is added and mixed until homogeneous. The lauramine oxide is added and mixed until homogeneous. The cocamide DEA is then added and mixed until homogeneous. The SD 40 Alcohol is then milled with the above mixture until homogeneous. The PVP/VA polymer, dimethicone copolyol, octyl salicylate, keratin amino acids, and perfume are then each in turn mixed into the composition. The resulting hairspray provides improved hair conditioning and volumizing benefits with a softer feeling hair hold.

What is claimed is:

1. A hair care composition comprising from about 0.05% to about 10.0% of a nonrigid silicone gum having a viscosity of from about 100,000 centistoke to about 300,000,000 centistoke; said gum having dispersed therein from about 0.01% to about 8.0%, by weight of the composition, of unsolubilized particulate matter which will not interact with the silicone gum.

2. The composition of claim 1 wherein the nonrigid silicone gum comprises from about 0.05% to about 7.0% of the composition and the unsolubilized particular matter comprises from about 0.01% to about 5.0% of the composition.

3. The composition of claim 2 wherein the viscosity of the nonrigid silicone gum is from about 1,000,000 centistoke to about 20,000,000 centistoke.

4. The composition of claim 3 wherein the unsolubilized particulate matter is selected from the group consisting of octyl acrylamide/acrylate/butylaminoethyl methacrylate copolymer; aluminum starch octenyl succinate; polyvinyl methyl ether maleic anhydride copolymer; acrylate/acrylamide copolymer; vinyl acetate/crotonic acid copolymer; titanium dioxide; calcium carbonate; talc and mixtures thereof.

5. The composition of the claim 4 wherein the unsolubilized particular matter has an average particle size of from about 0.1μ to about 15.0μ.

6. The composition of claim 5 wherein the nonrigid silicone gum is polydimethyl siloxane gum having a viscosity of from about 1,000,000 centistoke to about 20,000,000 centistoke.

7. The composition of claim 6 having a pH of from about 3 to about 7.

8. The composition of claim 7 wherein the unsolubilized particulate matter is an octylacrylamide/acrylate/butylaminoethyl methacrylate copolymer having a particle size of from about 0.15μ to about 2.0μ.

9. The composition of claim 8 which additionally comprises from about 0.01% to about 10% of a volatile silicone solvent.

10. The composition of claim 9 wherein the volatile silicone solvent is a cyclic silicone containing from about 3 to about 7 silicon atoms.

11. The composition of claim 10 wherein the volatile silicone solvent is cyclomethicone and is present at a level of from about 0.05% to about 5% of the composition.

12. The composition of claim 11 which additionally comprises from about 0.01% to about 10% of a silicone resin.

13. A hair care composition according to claim 12 wherein the nonrigid silicone gum is a polydimethyl siloxane gum having a viscosity of from about 1,000,000 centistoke to about 20,000,000 centistoke and the unsolubilized particulate material is an octylacrylamide/acrylate/butylaminoethyl methacrylate copolymer having a particle size of from about 0.5μ to about 2.0μ.

14. A hair care composition according to claim 1 wherein the nonrigid silicone gum is a polydimethyl siloxane gum having a viscosity of from about 1,000,000 centistoke to about 20,000,000 centistoke and the unsolubilized particulate material is an octylacrylamide/acrylate/butylaminoethyl methacrylate copolymer having a particle size of from about 0.15μ to about 2.0μ.

15. A hair care composition according to claim 14 in the form of a hair tonic which additionally comprises from about 0.25% to about 7.5% of an emulsifying agent.

16. A hair care composition according to claim 4 in the form of a shampoo which additionally comprises from about 10% to about 30% of a synthetic surfactant or mixtures thereof.

17. A hair care composition according to claim 16 wherein the synthetic surfactant is selected from the group consisting of alkyl sulfates, ethoxylated alkyl sulfates, and mixtures thereof.

18. A hair care composition according to claim 17 which comprises from about 0.1% to about 4.0% of the nonrigid silicone gum and from about 0.01% to about 1.0% of the unsolubilized particulate matter.

19. A hair care composition according to claim 14 in the form of a conditioner which additionally comprises from about 0.1% to about 10.0% of a lipid vehicle material and from about 0.05% to about 5.0% of a cationic surfactant.

20. A hair care composition according to claim 19 wherein the cationic surfactant is a quarternary ammonium salt.

21. A hair care composition according to claim 20 wherein the lipid vehicle material is selected from the group consisting of cetyl alcohol, stearyl alcohol, cetyl palmitate, glyceryl monostearate, and mixtures thereof.

22. A hair care composition according to claim 21 which comprises from about 0.05% to about 2.0% of the nonrigid silicone gum and from about 0.01% to about 0.5% of the unsolubilized particulate matter.

23. A hair care composition according to claim 14 in the form of a hair spray, which additionally comprises from about 0.25% to about 7.5% of an emulsifying agent.

24. The hairspray composition of claim 23 wherein the emulsifying agent is a material which will allow for the formation of a microemulsion of the silicone gum material in the hairspray composition.

25. The hairspray composition of claim 24 wherein the emulsifying agent is selected from the group consisting of anionic, cationic, nonionic surfactants and mixtures thereof.

26. The hairspray composition of claim 25 wherein the emulsifying agent is selected from the group consisting of combinations of anionic and nonionic surfactants and combinations of cationic and nonionic surfactants.

27. The hairspray composition of claim 26 wherein the emulsifying agent comprises a combination of lauramide oxide and cocamide DEA.

28. A hair care composition according to claim 14 in the form of a mousse.

29. A hair care composition according to claim 14 in the form of a gel.

30. A process for making the hair care composition of claim 1 comprising mixing the particulate matter and the silicone gum until the particulate matter is homogeneously dispersed in the gum and has a particle size of from about $0.15\mu$ to about $2\mu$ and formulating the mixture into a hair care composition selected from the group consisting of tonics, shampoos, conditioners, mousses, gels, and hairsprays.

* * * * *

UNITED STATES PATENT AND TRADEMARK OFFICE
CERTIFICATE OF CORRECTION

PATENT NO. : 4,983,383
DATED : January 8, 1991
INVENTOR(S) : Richard C. Maksimoski It is certified that error appears in the above-indentified patent and that said Letters Patent is hereby corrected as shown below:

*Column 24, line 34, "0.5µ" should read "--0.15µ--*

Signed and Sealed this

Thirty-first Day of December, 1996

Attest:

BRUCE LEHMAN

*Attesting Officer*  *Commissioner of Patents and Trademarks*